US005595562A

United States Patent [19]
Grier

[11] Patent Number: 5,595,562
[45] Date of Patent: Jan. 21, 1997

[54] MAGNETIC ENTERAL GASTROSTOMY

[75] Inventor: Jonathan F. Grier, Shreveport, La.

[73] Assignee: Research Corporation Technologies, Inc., Tucson, Ariz.

[21] Appl. No.: 337,103

[22] Filed: Nov. 10, 1994

[51] Int. Cl.$^6$ .................................................. A61B 17/11
[52] U.S. Cl. .............................................. 600/12; 600/115
[58] Field of Search .................................. 600/12, 15, 29, 600/30, 32; 604/48, 49, 54; 128/898

[56] References Cited

U.S. PATENT DOCUMENTS 3,952,726  4/1976  Hennig et al. ............................ 600/32
5,096,763  3/1992  Ogata et al. ............................. 600/12

FOREIGN PATENT DOCUMENTS

1725851A1  1/1990  U.S.S.R. .
1708313A1  1/1992  U.S.S.R. .

Primary Examiner—Angela D. Sykes
Assistant Examiner—Samuel Gilbert
Attorney, Agent, or Firm—Greenlee, Winner and Sullivan, P.C.

[57] ABSTRACT

A method of performing a gastrostomy by ischemia-induced tissue remodeling. To accomplish this, a small intragastric disk is magnetically coupled to a larger disk on the outside of the abdominal wall. The attractive magnetic force acting on the two disks occludes blood flow to the intervening tissue. The ensuing local ischemia results in infarction and resorption of that tissue. As the tissue is resorbed, the smaller intragastric disk is drawn toward the larger disk on the outside of the abdominal wall creating a stoma in its path and leaving the stomach adherent to the abdominal wall around the perimeter of the smaller disk.

27 Claims, 1 Drawing Sheet

MAGNETIC ENTERAL GASTROSTOMY

The present invention relates to the practice of medicine and specifically to the non-surgical formation of a gastrostomy by ischemia-induced tissue remodeling.

BACKGROUND OF THE INVENTION

Gastrostomy is defined as the establishment of a fistulous (i.e., acquired communication between a hollow structure and the exterior) opening (stoma) into the stomach (gastrostoma), with an external opening in the skin; usually for artificial feeding. It is one of the oldest operations performed, having appeared in writings as early as 1849. The usual reason for performing the operation in current practice is the patient's inability to tolerate an oral diet while having a functional gastrointestinal tract and a meaningful life expectancy. Although usually performed because of neurologic impairment, the list of reasons for gastrostomy continues to increase.

With refinements in surgical and anesthetic technique, surgical gastrostomy has become safe in spite of the generally debilitated population in whom it is performed. Additionally, several advantages over surgical methods have been provided by the introduction of the percutaneous endoscopic gastrostomy. Further, the recent explosion of laparoscopic technology has prompted minimally invasive placement of gastrostomies even for patients who may not be candidates for percutaneous endoscopic gastrostomies.

However, even with their popularity, the newer gastrostomy techniques still have significant shortcomings. Present technology requires surgery, laparoscopy, endoscopy, or percutaneous puncture (depending on the method used) as well as anesthesia (general, intravenous, local), antibiotic coverage, post-procedure analgesics, and delayed refeeding after the procedure.

Use of magnets in surgery has been previously reported. A method for cholecystogastrostomy involving magnetic compression was disclosed in Russian patent publication No. 1,708,313, published Jan. 30, 1992. Annular magnets were implanted endoscopically in the gall bladder via a temporary cholecystostomy and into the stomach via the oropharynx or an axial drainage catheter. The catheter simultaneously served a decompression function in patients with mechanical jaundice (cholestasis). After the anastomosis had been created, the drain was removed, together with the magnets. The complex procedure required perforation of the anterior abdominal wall, the anterior wall of the stomach, and an incision in the floor of the gall bladder.

Russian patent publication No. 1,725,851, published Apr. 4, 1992, discloses a device and surgical procedure for forming an intestinal anastomosis for treatment of large intestine obstruction. The device includes ring-shaped magnets and a forus-shaped guide, which is surgically implanted to aid in centering the magnets and reducing the risk of anastomotic incompetence.

SUMMARY OF THE INVENTION

The present invention involves the formation of a gastrostoma by ischemia-induced tissue remodeling. To accomplish this, a small intragastric magnetic disk is coupled to a larger magnetic disk on the outside of the abdominal wall. The attractive magnetic force acting on the two disks is sufficient to occlude blood flow to the intervening tissue. The ensuing local ischemia results in infarction and resorption of that tissue. As the tissue is resorbed, the smaller intragastric disk is drawn toward the larger disk on the outside of the abdominal wall creating a stoma in its path and leaving the stomach adherent to the abdominal wall around the perimeter of the smaller disk. This technique obviates surgery, laparoscopy, endoscopy, percutaneous puncture, anesthetics, antibiotics, and analgesics. The stomach can also be used for feeding continuously while the gastrostoma forms. The technique is termed magnetic enteral gastrostomy (MEG) herein.

BRIEF DESCRIPTION OF THE DRAWING

The above-mentioned and other features and objects of the invention and the manner of attaining them will become more apparent and the invention itself will best be understood by reference to the following description of embodiments of the invention taken in conjunction with the accompanying drawing, a brief description of which follows.

DETAILED DESCRIPTION

Figure 1:
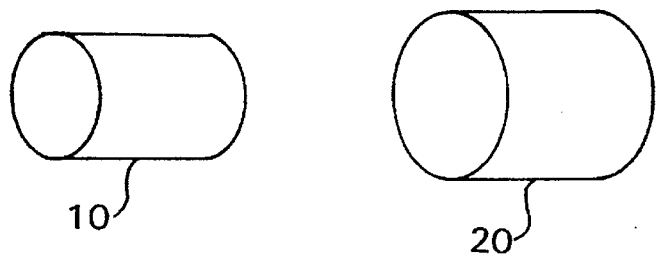
FIG. 1 is a diagram of a small magnetic disk for intragastric use and a larger magnetic disk for external use.

In the drawing, like reference numerals indicate like features; and, a reference numeral appearing in more than one figure refers to the same element. The drawing and the following detailed description show a specific embodiment of the invention. Numerous specific details including materials, dimensions, and products are provided to enable a more thorough understanding of the invention. However, it will be obvious to one skilled in the art that the present invention may be practiced without these specific details.

FIG. 1 is a diagram showing the two magnetic disks used to perform a gastrostomy. Disk 10 is a magnetized neodymium cylinder one-half inch in diameter by one-half inch in length. Disk 20 is a magnetized neodymium cylinder one inch in diameter by one-half inch in length. Both magnets are polarized such that the axis of disk 10 aligns itself in a direction perpendicular to a flat surface of disk 20 when disk 10 is attracted to disk 20. The magnets may be polarized radially or axially, although radial polarization is preferred.

Figure 2:
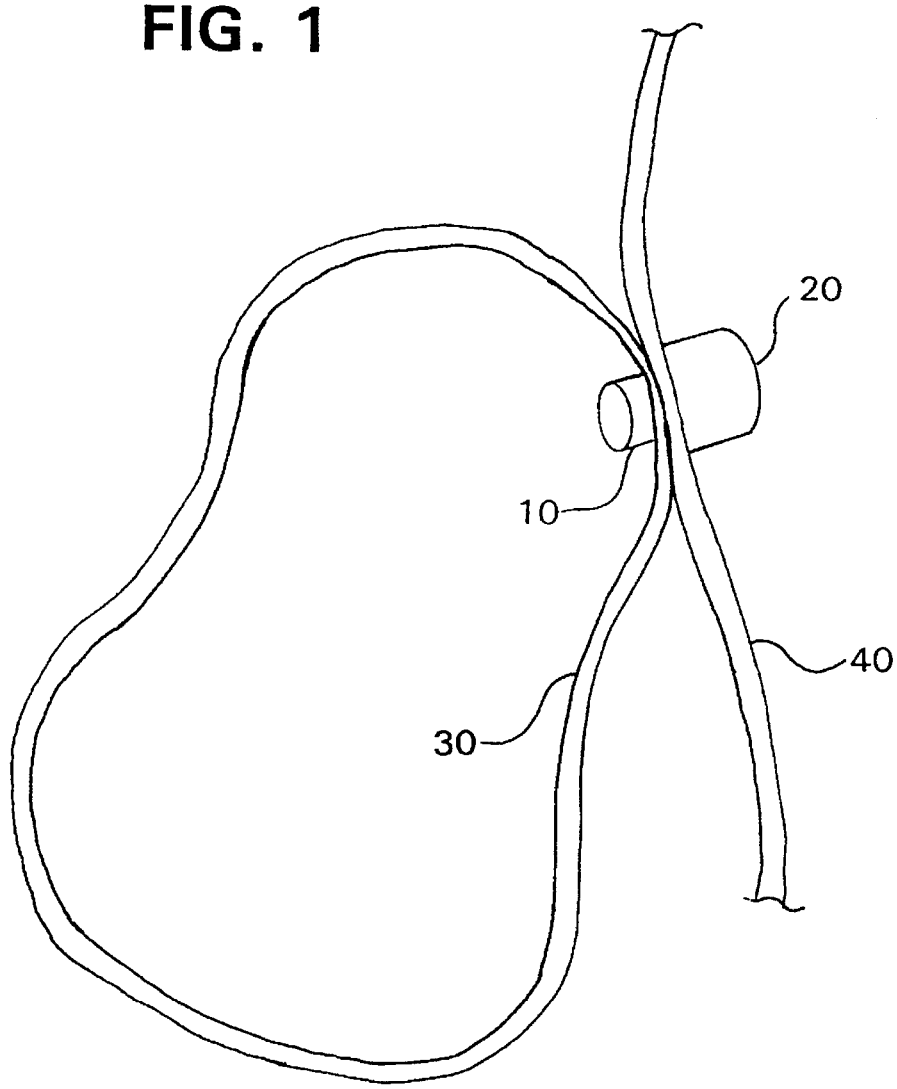
FIG. 2 is a diagram showing magnetic disks in place to form a gastrostomy.

FIG. 2 is a diagram showing the magnetic disks in place to perform a gastrostomy. Disk 10 is located inside the stomach 30 adjacent to abdominal wall 40. Disk 20 is located on the outside of abdominal wall 40 as close as possible to disk 10. Disks 10 and 20 are held in place by magnetic attraction through the stomach and abdominal walls between the disks.

To begin the process of a magnetic enteral gastrostomy (MEG), disk 10 is introduced into the stomach adjacent to the abdominal wall by either swallowing it, affixing it to the tip of a nasogastric tube, or endoscopically with a gastroscope, as appropriate for the patient's condition. Then, disk 20 is placed on the outside of the abdominal wall opposite disk 10 whereupon the magnetic field causes the disks to be drawn together squeezing the stomach and abdominal walls together between the disks. Following placement of the disks, appropriate dressings are applied to prevent inadvertent removal of disk 20.

With time, the intragastric disk 10 migrates through the ischemic tissue of the stomach and abdominal walls, clamped between the magnets, forming a gastrostoma in which the gastric body is adherent to the anterior abdominal wall. The adherence is a characteristic which the MEG has in common with surgical and percutaneous techniques and which minimizes the risk of intraperitoneal leakage. MEG is operative whenever the attractive force between internal and external magnets is sufficiently strong to result in some degree of local ischemia of the tissue between the magnets. Gradual tissue thinning between the magnets then results in stronger attraction and eventually complete ischemia. If the magnets have sufficient attractive force to engage one another when the internal magnet is in a patient's stomach and the external magnet is placed on the patient's outer abdominal wall, a sufficient degree of ischemia is obtained. Preferred magnets are neodymium magnets, but other magnets, particularly those of rare earth alloys, may be used provided the attractive force is sufficient to produce the requisite local ischemia.

While the invention has been described above with respect to specific embodiments, it will be understood by those of ordinary skill in the art that various changes in form and details may be made therein without departing from the spirit and scope of the invention. For example, although less desireable, the gastrostomy could be performed by disks of equal or similar diameters whereby both disks would migrate toward each other, or by placing the smaller disk on the outside of the abdomen whereby the smaller disk would migrate toward the larger intragastric disk. Also, for example, the shape of the larger disk, particularly if placed outside of the abdomen, is less critical than that of the smaller disk and could have shapes other than circular, including elongated or rectangular flat plates (with an appropriate magnetic field distribution).

The tissue remodeling induced by ischemia can be applied in other ways. For example, an intestinal by-pass for treatment of obesity can be made using magnetically-induced ischemia. Other applications include cystostomies, arteriovenous fistulas, tracheostomies, and the like.

EXAMPLES

Materials and Methods:

One male and two female pigs (*Sus scrofa domesticus*), aged 2 to 3 months and weighing 15 to 20 kg were studied. Criteria of the National Research Council for care and use of laboratory animals in research were carefully followed, and the experimental protocol was approved by the Institutional Review Board of the Louisiana State University School of Medicine in Shreveport. After an overnight fast each animal was sedated with intramuscular xylazine (2 mg/kg) and ketamine (10 mg/kg). Pig #1 underwent complete esophagogastroduodenoscopy (EGD) with a video gastroscope (Olympus GIF100), while in the left lateral decubitus position. A Steigman-Goff overtube (Bard, Tewksbury Mass.) was placed in the esophagus over the gastroscope, and the gastroscope was removed.

A disc-shaped, neodymium magnet (Adams Magnetic Products, Apopka Fla.), measuring ½ inch diameter by ½ inch thick was placed in the overtube and pushed through with the gastroscope. Another disc-shaped neodymium magnet, measuring 1 inch diameter by ½ inch thick was used to probe the left upper quadrant while the pig remained in the left lateral decubitus position. A palpable click occurred as the internal and external magnets engaged, leaving the external magnet suspended on the left upper quadrant. The fixation of the internal magnet in the gastric body was confirmed endoscopically in the case of pig #1. The same procedure was followed for pigs #2 and 3 except the endoscope was only used to pass the overtube and push the magnet through, and the external magnet on pig #2 measured 1 inch diameter by 1 inch thick. Neither pig #2 nor 3 underwent EGD nor endoscopic confirmation of magnet placement.

The abdomen was wrapped circumferentially with gauze and 2 inch wide cloth tape to prevent removal of the external magnet. For the pig's comfort, the tape only contacted the skin just above and below the gauze. After sedation, the procedure required roughly ten minutes. Each pig recovered uneventfully, and there were no procedure-related complications. Dressings were changed every third day for inspection of the site and application of a secure but non-constricting dressing. As the pigs grew, sedation became necessary as described above in order to change dressings.

RESULTS

All three pigs thrived with the magnets in situ. They consumed a regular chow diet, gained weight, and exhibited no evidence of illness. On the morning of day #12 post magnet placement, pig #1 removed his dressing and the external magnet was on the floor of his pen. After sedation, examination revealed a tract where the magnet had been. A "button" gastrostomy tube (Bard, Tewksbury, Mass.) passed easily through the tract, and intragastric location of the "button" tip was documented endoscopically. The smaller internal magnet was never found, but x-ray confirmed it was not in the pig. Possibly it was inadvertently discarded during cleaning of the pen. The gastrostomy tube remained in place for one week, until pig #1 again removed his dressing along with the gastrostomy tube. Five days later, after sedation, pig #1 was sacrificed with intracardiac Beuthanasia-$D^R$ (1 ml/10 kg, Schering-Plough, Kenilworth N.J.). With gentle probing, the gastrostomy was intubated with a 20 F Foley catheter. Necropsy revealed no intraperitoneal leakage or perforation. A well-formed gastrostoma in the gastric body was firmly adherent to the anterior abdominal wall. Intragastric placement of the catheter was confirmed.

With refinements in the technique, pigs #2 and 3 were kept from removing their dressings. When the dressings were changed on day #11 post magnet placement, the smaller internal magnet of pig #2 was visible and adherent to the larger external magnet with a thin intervening eschar. The magnet/eschar complex was easily removed, disclosing a roughly ¾ inch diameter gastrostoma, through which a balloon tip gastrostomy tube (Bard, Tewksbury Mass.) was placed. The dressing of pig #3 was changed on day #10 post magnet placement, and again the magnet/eschar complex, occluding a roughly ¾ inch gastrostoma, was found. The same procedure was followed as in pig #2.

Each pig thrived after gastrostoma formation, eating all available food and gaining weight. However, on the afternoon of day #4 post gastrostomy tube placement, pig #2 became acutely ill with respiratory distress and expired suddenly. Necropsy did not identify a cause of death and revealed a well-formed gastrostoma in the gastric body, firmly adherent to the anterior abdominal wall. The tip of the gastrostomy tube was intragastric and there was no intraabdominal sepsis, perforation or leakage. Pig #3 was sacrificed in the manner described previously on day #5 post gastrostomy tube placement. Necropsy revealed a well-formed gastrostoma in the gastric body adherent to the anterior abdominal wall. As in pigs #1 and 2, there was no leakage or perforation, and intragastric placement of the gastrostomy tube was confirmed.

Microscopic examination of hematoxylin and eosin stained longitudinal sections of the gastrostoma from pig #1 showed gastric mucosa internally and stratified squamous epithelium externally, connected by a tract lined with granulation and fibrous tissue. There was no abscess formation and only slightly inflammatory infiltrate (FIG. 2). In each case the gastrostoma that was initially ¾ inch diameter quickly contracted around the tube it contained.

DISCUSSION

A magnetic enteral gastrostomy (MEG) was created in each of three pigs. As blood flow to the tissue compressed between the magnets is occluded, the tissue becomes ischemic and infarcted. Without being bound by a specific mechanism of action, it appears that MEG most likely involves resorption of the infarcted tissue, which (although dead) still has structural integrity. Blood supply to a small rim of tissue surrounding the smaller magnet is likewise compromised, resulting in a gastrostoma that is slightly larger than the smaller magnet. Furthermore, compression in excess of what is required to occlude blood flow does not appear to accelerate gastrostomy formation, as in the case of pig #2 whose external magnet was twice as thick as the external magnets on pigs #1 and #3. Therefore, magnetic attraction between the internal and external magnets should be strong enough to produce local ischemia of the tissues between the magnets, but need be no stronger.

The adherence of the gastrostoma to the anterior abdominal wall is a characteristic MEG has in common with surgical gastrostomies and newer percutaneous endoscopic techniques. This minimizes the risk of intraperitoneal leakage should the gastrostomy tube be pulled out, as was the case in pig #1. Because the gastric lumen does not communicate with the peritoneal cavity, antibiotic coverage is not necessary.

Except for an overnight fast prior to magnet placement, the pigs were fed orally as the gastrostomy formed. In fact, the extrusion of pig chow upon removal of the magnet/eschar complex was the first indication of a gastro-cutaneous fistula. The ability to use the stomach continuously while the magnets are in place is an advantage over other techniques. Though there is no objective way to evaluate pain in pigs, no change in their behavior or eating pattern after magnet placement was observed. Preparations were made to administer analgesics, local anesthesia or euthanize as needed, but this was unnecessary. This apparent absence of procedure-related pain is another advantage.

The results demonstrate that gastrostomies can be formed by ischemia-induced tissue remodeling, avoiding surgery and percutaneous punctures. MEG does not require antibiotic coverage, post-procedure analgesics or prolonged fasting. Though a gastroscope was employed in the experimental protocol, the technique can be accomplished non-endoscopically. The process is feasible with a smaller internal magnet than the size used in this example. A smaller internal magnet would avoid an excessively large gastrostoma and make placement of the internal magnet as simple as swallowing it or affixing it to the tip of a nasogastric tube. Indeed, patients who require gastrostomy due to inability to tolerate an oral diet may benefit from nasogastric tube feeding while the MEG is taking place.

Magnetic enteral gastrostomy can provide inexpensive, safe, non-invasive, permanent enteral access. MEG can be performed safely without surgery., laparoscopy, endoscopy, anesthesia, antibiotics or analgesics on an outpatient basis. These advantages of MEG can significantly reduce the cost of making gastrostomies. Using ischemia-induced tissue remodeling to create fistulas is also advantageous for clinical and research purposes, both in the gastrointestinal tract as well as other organ systems.

I claim:

1. A method for performing a gastrostomy, said gastrostomy producing an opening from the interior of a patient's stomach through the patient's stomach wall and abdominal wall, comprising the steps of:

introducing a first magnet into the stomach;

placing said first magnet on the stomach wall adjacent to the abdominal wall;

placing a second magnet on the outside of the abdominal wall opposite, and relative to, said first magnet whereby said first magnet and said second magnet are drawn together compressing a portion of the stomach wall and a portion of the abdominal wall to produce local ischemia between said first magnet and said second magnet; and allowing said first magnet and said second magnet to remain in place for a time sufficient to form a tract substantially through the stomach wall and the abdominal wall thereby forming a gastrostoma adherent to the abdominal wall.

2. The method of claim 1 wherein at least one of said first and second magnets is made of neodymium.

3. The method of claim 1 wherein said first magnet is cylindrical in shape, having a diameter and a longitudinal axis, and said second magnet has a flat surface, which is larger than the diameter of said first magnet, for placing against the abdominal wall.

4. The method of claim 3 wherein said first magnet and said second magnet have magnetic orientations and strengths which tend to align said axis of said first magnet perpendicular to said flat surface of said second magnet.

5. The method of claim 4 wherein at least one of said first and second magnets is made of neodymium.

6. The method of claim 4 wherein at least one of said first and second magnets is made of rare earth alloy.

7. The method of claim 1 wherein said step of introducing said first magnet into the stomach is accomplished by swallowing said first magnet.

8. The method of claim 7 wherein said step of placing said first magnet on the stomach wall adjacent to the abdominal wall is accomplished with the aid of gravity.

9. The method of claim 1 wherein said steps of introducing said first magnet into the stomach and placing said first magnet on the stomach wall adjacent to the abdominal wall are accomplished by use of endoscopy.

10. The method of claim 1 wherein said steps of introducing said first magnet into the stomach and placing said first magnet on the stomach wall adjacent to the abdominal wall are accomplished by use of a nasogastric tube.

11. The method of claim 1 wherein at least one of said first and second magnets is made of rare earth alloy.

12. Apparatus for performing a gastrostomy, said gastrostomy producing an opening from the interior of a patient's stomach through the patient's stomach wall and abdominal wall, comprising:

a first magnet adapted to be placed inside the stomach on the stomach wall adjacent to the abdominal wall;

a second magnet adapted to be placed on the outside of the abdominal wall opposite, and relative to, said first magnet whereby said first magnet and said second magnet are drawn together compressing a portion of the stomach wall and a portion of the abdominal wall to produce local ischemia of tissue between said first magnet and said second magnet: and external means, adapted to be placed outside the abdominal wall, for keeping said second magnet in place for a time sufficient to form a tract substantially through said stomach wall and said abdominal wall thereby forming a gastrostoma adherent to said abdominal wall.

13. The apparatus of claim 12 wherein said external means for keeping said second magnet in place is a dressing applied to prevent inadvertent removal of said second magnet.

14. The apparatus of claim 12 wherein at least one of said first and second magnets is made of neodymium.

15. The apparatus of claim 12 wherein at least one of said first and second magnets is made of rare earth alloy.

16. The apparatus of claim 12 wherein said first magnet is cylindrical in shape, having a longitudinal axis, and said second magnet has a flat surface, which is larger than the diameter of said first magnet, for placing against the abdominal wall.

17. The apparatus of claim 16 wherein said first magnet and said second magnet have magnetic orientations and strengths which tend to align said axis of said first magnet perpendicular to said flat surface of said second magnet.

18. The apparatus of claim 17 wherein at least one of said first and second magnets is made of neodymium.

19. The apparatus of claim 17 wherein at least one of said first and second magnets is made of rare earth alloy.

20. The apparatus of claim 12 wherein said first and second magnets are in the form of magnetic disks.

21. The apparatus of claim 20 wherein said first magnetic disk and said second magnetic disk have magnetic orientations and strengths which attract a flat surface of said first magnetic disk to a flat surface of said second magnetic disk.

22. The apparatus of claim 21 wherein at least one of said first and second magnetic disks is made of neodymium.

23. The apparatus of claim 21 wherein at least one of said first and second magnets is made of rare earth alloy.

24. A kit for performing a gastrostomy, said gastrostomy producing an opening from the interior of a patient's stomach through the patient's stomach wall and abdominal wall, comprising: a first magnet, adapted to be placed in the patient's stomach; a second magnet, said magnets having sufficient attractive force to engage one another when said first magnet is in the stomach and said second magnet is placed on the outside of the abdominal wall, opposite and relative to said first magnet; and external means, adapted to be placed outside the abdominal wall, for keeping said second magnet in place.

25. The kit of claim 24 wherein said external means for keeping said second magnet in place is a dressing applied to prevent inadvertent removal of said second magnet.

26. The kit of claim 24 wherein at least one of said first and second magnets is made of neodymium.

27. The kit of claim 24 wherein at least one of said first and second magnets is made of rare earth alloy.

* * * * *